(12) United States Patent
Shoham et al.

(10) Patent No.: US 10,076,385 B2
(45) Date of Patent: Sep. 18, 2018

(54) METHOD AND APPARATUS FOR ALERTING A USER TO SENSED LATERAL FORCES UPON A GUIDE-SLEEVE IN A ROBOT SURGICAL SYSTEM

(71) Applicant: MAZOR ROBOTICS LTD., Caesarea (IL)

(72) Inventors: Moshe Shoham, Hoshaya (IL); Eli Zehavi, Haifa (IL)

(73) Assignee: MAZOR ROBOTICS LTD., Caesarea ( * ) Notice: Subject to any disclaimer, the term of this patent is extended or adjusted under 35 U.S.C. 154(b) by 707 days.

(21) Appl. No.: 14/563,983

(22) Filed: Dec. 8, 2014

(65) Prior Publication Data

US 2015/0209056 A1    Jul. 30, 2015

Related U.S. Application Data

(60) Provisional application No. 61/913,328, filed on Dec. 8, 2013.

(51) Int. Cl.

| | | |
|---|---|---|
| A61B 17/17 | (2006.01) | |
| A61B 19/00 | (2006.01) | |
| A61B 34/30 | (2016.01) | |
| A61B 90/11 | (2016.01) | |
| A61B 17/00 | (2006.01) | |
| A61B 90/00 | (2016.01) | |

(52) U.S. Cl.
CPC .......... *A61B 19/2203* (2013.01); *A61B 34/30* (2016.02); *A61B 90/11* (2016.02); *A61B 17/1703* (2013.01); *A61B 17/1707* (2013.01); *A61B 17/1757* (2013.01); *A61B 2017/00119* (2013.01); *A61B 2090/064* (2016.02)

(58) Field of Classification Search
CPC . A61B 17/17; A61B 17/1732; A61B 17/1703; A61B 17/1707; A61B 19/201; A61B 19/2203
See application file for complete search history.

(56) References Cited

U.S. PATENT DOCUMENTS

| | | | |
|---|---|---|---|
| 5,807,378 A | * | 9/1998 | Jensen ........................ B25J 3/04 403/316 |
| 6,837,892 B2 | | 1/2005 | Shoham |
| 7,646,161 B2 | | 1/2010 | Albu-Schaffer et al. |
| 8,469,963 B2 | | 6/2013 | Shoham |
| 2004/0106916 A1 | * | 6/2004 | Quaid .................... A61B 34/71 606/1 |
| 2012/0158011 A1 | | 6/2012 | Sandhu et al. |

FOREIGN PATENT DOCUMENTS

WO    WO2011014677    2/2011

* cited by examiner

*Primary Examiner* — Christopher Beccia
(74) *Attorney, Agent, or Firm* — Marc Van Dyke; Fourth Dimension IP

(57) ABSTRACT

Methods and apparatus for detecting or predicting surgical tool-bone skiving are disclosed. In some embodiments, the surgical tool is movably and/or snugly disposed within a guide-sleeve. In some embodiments, a magnitude of a lateral force between the surgical tool and the guide-sleeve is measured (e.g. by a force sensor or strain sensor). The present or future skiving may be detected or predicted according to the magnitude of the lateral force. In some embodiments, an alert signal is generated in response to the detecting or predicting of the skiving.

15 Claims, 16 Drawing Sheets

PRIOR ART

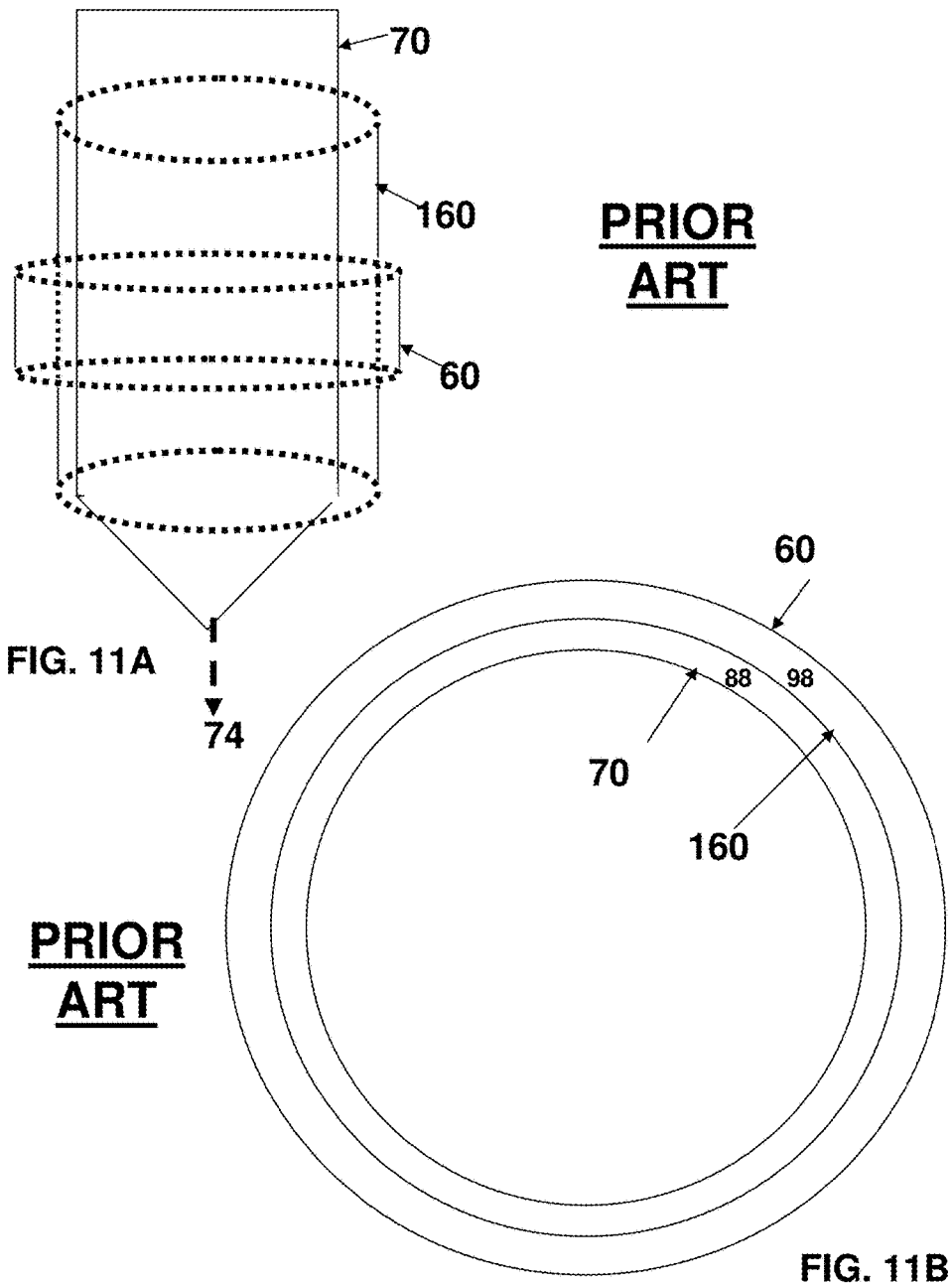

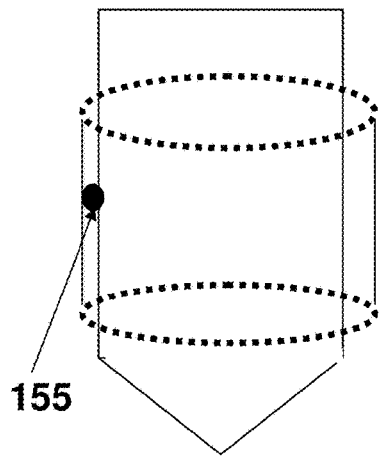
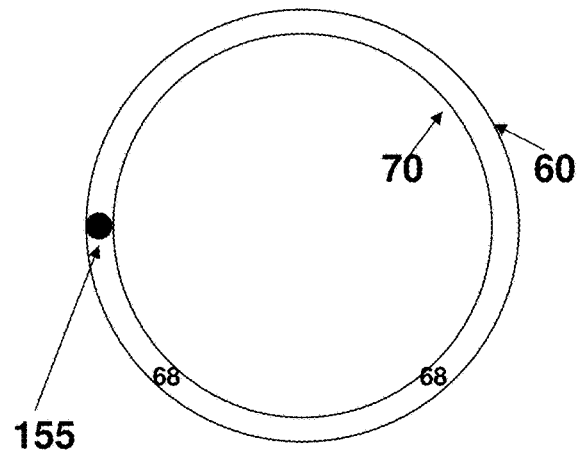
FIG. 13A          FIG. 13B
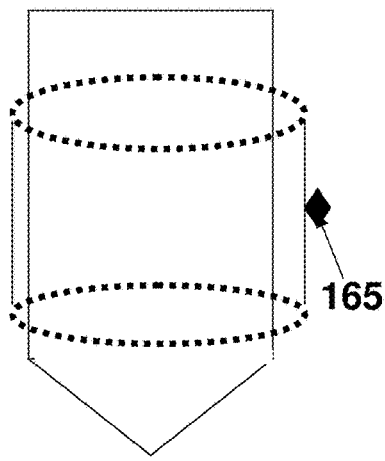
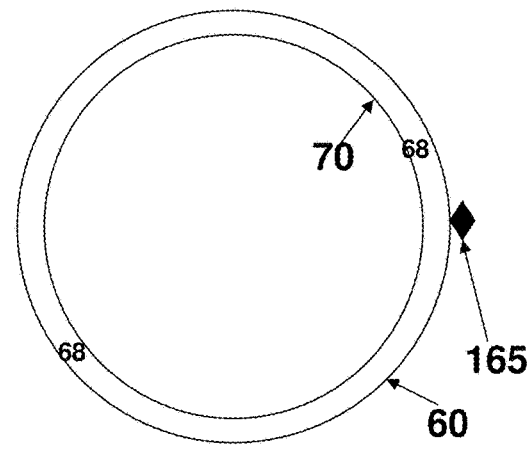
FIG. 13C          FIG. 13D

METHOD AND APPARATUS FOR ALERTING A USER TO SENSED LATERAL FORCES UPON A GUIDE-SLEEVE IN A ROBOT SURGICAL SYSTEM

CROSS-REFERENCE TO RELATED APPLICATIONS

This patent application claims the benefit of U.S. Provisional Patent Application No. 61/913,328 filed on Dec. 8, 2013, which is incorporated herein by reference in its entirety.

BACKGROUND

Bone-Mounted Robotic Surgery

U.S. Pat. No. 6,837,892 of one of the present inventors, discloses a miniature surgical robot and a method for using it. The miniature surgical robot attaches directly with the bone of a patient. Two-dimensional X-ray images of the robot or a target on the robot base, on the bone are registered with three-dimensional images of the bone. This locates the robot precisely on the bone of the patient. The robot is then directed to pre-operative determined positions based on a pre-operative plan by the surgeon. The robot then moves to the requested surgical site and aligns a sleeve through which the surgeon can insert a surgical tool.

FIGS. 1-4 and 6-8 are prior-art figures that are all taken from U.S. Pat. No. 6,837,892

FIGS. 1A-1B illustrates an image guided, robot assisted, surgical system. Included in this system generally, as shown in FIGS. 1A-1B, is a bone attached surgical robot 30; a control unit 10 that matches data from CT scans and C-arm images to locate robot 30 on the patient's bone and directs the robot according to pre or intra-operative plan Control unit 10 generally includes a CPU and user interface communicating with display 20 and robot 30.

As an example of bone-mounted surgical robot see FIG. 2 where a robot, 30, directs a sleeve, 60, along a pre-planned trajectory through which the surgeon insert the surgical tools.

Clamp 40 (illustrated in FIG. 2) is an example of one embodiment according to the invention by which a robot may be attached to a bone for assisting in a surgical procedure. Other attachment devices can also be incorporated with a robot such as, for example, K-wire connections. FIG. 8 illustrates such a K-wire connection. K-wires 950 are inserted into the bone by standard surgical procedures. Robot base 35 contains an elongated slot through which K-wires 950 are inserted. Screw 960 can then be turned and tighten pinch plate 970 against robot base 35 pinching K-wires 950 between pinch plate 970 and robot base 35 holding robot 30 tight with respect to K-wires 950 and bone 50.

FIG. 5 is a close-up of sleeve 60 and surgical instrument 70 deployed therein. The guide sleeve 60 is firmly held by the robot arm 72 in its predetermined pose, such that the surgical drill 70 enters the bone 75 at the desired location and the desired angle determined by the robot pose. If the drill 70 enters the bone at approximately normal incidence, there is little tendency for it to skive. On the other hand, if the surgical plan requires that the drill enters the bone at a non-normal incidence, as shown in FIG. 5, and which may commonly occur in spinal surgery because of the topographical nature of the surface of the vertebrae, there is a tendency for the drill to skive away 76 from the point of entry 77. Since the robot generally holds the sleeve firmly, the drill trajectory itself will not usually change, but when the lateral component of thrust resulting from the non-normal entry angle becomes larger than a certain level, this may cause the bone to move or flex away from the drill center line, thus resulting in an inaccurately positioned bore. The stability of the robot mount to which arm 72 is ultimately attached, may also contribute to the loss of accuracy due to the skiving effect. Some embodiments of the present invention are useful for overcoming this situation.

FIGS. 9A-9B are schematic drawing of the element in FIG. 5 including sleeve 60 having sleeve axis 62. Also illustrated in FIGS. 9A-9C is surgical instrument 70 having instrument axis 72 which (i) is an elongate axis of the surgical instrument 70 and/or (ii) an axis defined by and co-linear with an "operation direction" 74 of the surgical instrument—i.e. a direction at which the surgical instrument operates—e.g. a drilling direction in the case of a drill. As shown in FIG. 9C (side view), surgical instrument 70 may be snugly disposed within sleeve 60 so that operation direction 74 and/or a direction of axis 72 is determined by a direction of the sleeve 60 (i.e. defined as the direction of sleeve axis 62). As shown in FIG. 9C, the surgical instrument 70 is aligned with sleeve 60—i.e. so that sleeve axis 62 and the instrument axis 72 of surgical instrument 70 are aligned with each other.

FIG. 9D is a top view the system of FIG. 9C illustrating the annular region 68 between the instrument 70 and sleeve 60—since the instrument is 'snugly' disposed within sleeve 60, this annular region is relatively thin—i.e. the tolerances are tight.

As illustrated in FIGS. 10-11, in some embodiments, there is an inner sleeve 160 having sleeve axis 162 that is disposed within outer sleeve 60—for example, snugly disposed therein so that respective axes 62, 162 are aligned. FIG. 11B illustrates a top view including annular regions 88 and 98.

One example of an inner sleeve is a surgical canulla 160—for example, as illustrated in FIG. 12 including knurled knob 120 at a proximal end, and a tapered distal end 130.

Skiving

When drilling into a bone, skiving may occur when the drilling instrument is not directed perpendicular to the bony surface—the instrument may skive or skip across the bony surface. Skiving is not limited to surgical drills. In another example, when a canulla device in contact with a bone slips along the surface of the bone, this also may be referred to as skiving.

A number of prior art patent documents disclose methods apparatus and methods for minimizing (or mitigating) a risk of skiving or an extent of skiving. This may occur by stabilizing an instrument upon the surface of the bone or by reducing the imparting of a skiving force from the instrument upon a surface of the bone. Examples of patent documents that disclose apparatus or methods for reducing skiving include WO2011014677 and U.S. Pat. No. 8,469,963 (of one of the present inventors).

SUMMARY OF EMBODIMENTS

A system for performing a surgical procedure at a surgical site comprises: a. a guide-sleeve defining axial and lateral directions; b. a surgical tool movably and/or snugly disposed within the guide-sleeve so that an alignment direction of the surgical tool is determined by that of the guide-sleeve; and c. a skiving-detector configured (e.g. when the guide-sleeve is in a position and/or orientation determined by the guidance system) to (i) detect or predict, in accordance with a magnitude of a lateral force between the surgical tool and the guide-sleeve or an indication thereof, present or future tool-bone skiving by the surgical tool, and (ii) generate an alert signal in a manner that is contingent upon a positive detecting or predicting of the skiving.

A system for performing a surgical procedure at a surgical site, the system comprises: a. a guide-sleeve defining axial and lateral directions; b. a surgical tool movably and/or snugly disposed within the guide-sleeve so that an alignment direction of the surgical tool is determined by that of the guide-sleeve; and c. a force sensor configured to measure (e.g. when the guide-sleeve is in a position and/or orientation determined by the guidance system) a lateral force between the surgical tool and the guide-sleeve or an indication thereof (for example, the force sensor may be configured to measure the lateral force or indication thereof in a manner that is substantially independent of a magnitude of an axial force between the surgical tool and the guide-sleeve); and e. an alert-signal-generator configured to generate an alert signal in a manner that is contingent upon a magnitude of the measured lateral force or indicator exceeding a force-threshold.

In some embodiments, the system further comprises a position/orientation controller operative to modify and/or regulate changes in a position and/or an orientation of the guide-sleeve; and In some embodiments, the position/orientation controller comprises a surgical robot.

In some embodiments, the position/orientation controller comprises a passive guidance system where mechanical force for moving and/or orienting the guide-sleeve is manually supplied.

In some embodiments, the position/orientation controller comprises a stereotactic system.

A method of warning a user of a risk of misalignment of a surgical instrument used to perform a surgical procedure at a surgical site comprises a. orienting and/or positioning a guide sleeve in a target direction and/or orientation; b. at a time when the surgical instrument is disposed within the guide sleeve, measuring a lateral force applied by an object (e.g. the surgical instrument within the guide sleeve) upon the guide sleeve or an indication of the lateral force; and c. contingent upon the results of the measuring indicating that the lateral force exceeds a force-threshold, generating an alert signal.

A method of performing a surgical procedure by a surgical instrument deployed within a guide-sleeve and directed along an orientation thereof, the method comprises a. orienting and/or positioning a guide sleeve in a target direction and/or orientation; b. at a time when the surgical instrument is disposed within the guide sleeve, measuring a lateral force applied by an object (e.g. the surgical instrument within the guide sleeve) upon the guide sleeve or an indication of the lateral force; and c. contingent upon the results of the measuring indicating that the lateral force is equal to at most a force-threshold, performing a surgical operation upon the patient using the surgical instrument deployed within the guide-sleeve.

In some embodiments, the surgical operation of step (c) is partly or entirely robotic.

In some embodiments, the surgical operation of step (c) is partly or entirely manual.

A method of preventing skiving or reducing a risk thereof comprises a. orienting and/or positioning a guide sleeve in a target direction and/or orientation; b. acquiring measurement data descriptive a likelihood of present or future skiving by a surgical instrument in contact with a bone of a patient and deployed within the guide-sleeve so as to be oriented by an orientation of the guide-sleeve; and c. generating an alert signal in a manner that is contingent upon the acquired measurement data that the likelihood of the present or future skiving by the surgical instrument exceeds a skiving-risk threshold.

A method of preventing skiving or reducing a risk thereof, the method comprises: a. orienting and/or positioning a guide sleeve in a target direction and/or orientation; b. acquiring measurement data descriptive a likelihood of present or future skiving by a surgical instrument in contact with a bone of a patient and deployed within the guide-sleeve so as to be oriented by an orientation of the guide-sleeve; and c. contingent upon the results of the measuring indicating that the likelihood of skiving is below a skiving-risk threshold, performing a surgical operation upon the patient using the surgical instrument as deployed within the guide-sleeve.

A method of preventing a deviation of a surgical tool from its planned trajectory or reducing a risk thereof comprises a. orienting and/or positioning a guide sleeve in a target direction and/or orientation; b. acquiring measurement data descriptive a likelihood of a present or future deviation, by a surgical instrument deployed within the guide-sleeve, from its planned trajectory; and c. generating an alert signal in a manner that is contingent upon the measurement data indicating that the likelihood of the present or future present or future deviation by the surgical instrument exceeds a risk threshold.

A method of preventing a deviation of a surgical tool from its planned trajectory or reducing a risk thereof comprises a. orienting and/or positioning a guide sleeve in a target direction and/or orientation; b. acquiring measurement data descriptive a likelihood of a present or future deviation, by a surgical instrument deployed within the guide-sleeve, from its planned trajectory; and c. contingent upon the results of the measuring indicating that the likelihood of skiving is below a threshold, performing a surgical operation upon the patient using the surgical instrument as deployed within the guide-sleeve.

In some embodiments, the orienting and/or positioning of the guide sleeve is performed robotically.

In some embodiments, the orienting and/or positioning of the guide sleeve is performed manually.

In some embodiments, the measurement data is acquired by measuring at least one force or moment, or an indication thereof, selected from the group consisting of: (i) a force upon the guide-sleeve; and (ii) a force upon an object mechanically coupled to the guide sleeve.

In some embodiments, the measurement data is acquired by measuring at least one lateral force, or an indication thereof, selected from the group consisting of: (i) a lateral force upon the guide-sleeve; and (ii) a lateral force upon an object mechanically coupled to the guide sleeve.

In some embodiments, the object is the surgical instrument or an inner sleeve within the guide-sleeve.

In some embodiments, further comprising an attachment member configured and dimensioned to mount the surgical robot on a bone associated with the surgical site, such that (i) the robot's position relative to said bone is unchanged with motion of the bone and/or (ii) the robot is supported in its entirety by said bone.

said attachment member comprises a robot receiving adaptor mounted on a bone attachment portion.

Alternatively, the surgical robot does not need to be mounted to and/or supported by the bone. In other examples, the surgical robot is mounted to and/or supposed by the bone.

Alternatively, the robot is not necessarily bone-mounted—for example, a bed-mounted, floor-mounted or ceiling-mounted robot or a robot supported in any other manner.

Also even with passive devices manually directed along the required trajectory the same problem might occur and hence the solution can be applied.

In some embodiments, said bone attachment portion comprises a clamp having at least two jaws shaped to mate with a specific bone configuration.

In some embodiments, said bone attachment portion comprises at least one wire configured and dimensioned to be received in bone holes.

In some embodiments, wherein said attachment member is either one of a bone clamp and or at least a pair of Kirschner-wires.

In some embodiments, the magnitude of the lateral force is indicative of at least one of a (i) a degree of bone flexibility which causes the robot to miss its target orientation because of the force—the more flexible the bone is, the more
and resulting deviation; and (ii) a degree of flexibility of the mount object upon which the surgical robot is mounted on the bone and resulting deviation.

Not wishing to be bound by theory, it is noted that there is a relationship between lateral force, flexibility and deviation—if the bone is flexible, even a small lateral force will cause a significant deviation. If the bone is not flexible, the deviation will be minimal or non-existent even when larger lateral forces are applied.

In some embodiments, the 'force threshold' or any other threshold related to generating the alert signal (or proceeding with a surgical procedure)—i.e. the minimal force or indication thereof required to generate an alert—may be a 'variable' or 'adaptive' threshold value depending on bone flexibility. For relatively flexible bones, a lower force threshold value (or indication thereof) may be selected. For more rigid bones, a higher value may be selected.

In some embodiments, the bone flexibility may be related to a presence or absence of osteoporosis—e.g. a lower force threshold value may be selected in situations where the surgical site is associated with an osteoporotic bone. Thus, in some embodiments, the method or system includes (i) estimating a degree of bone flexibility (e.g. in accordance with an assessment or indication of a presence or absence or degree of osteoporosis) and (ii) selecting an 'alert threshold' in accordance with the results of the estimating of the degree of bone flexibility.

In some embodiments, wherein the surgical tool is a surgical canulla.

In some embodiments, wherein the surgical tool comprises at least one of: (i) a plurality of teeth at a distal end thereof and (ii)

In some embodiments, wherein the surgical tool is selected from the group consisting of a drill, a reamer, a biopsy needle, forceps and an endoscope.

In some embodiments, the lateral force is at least partially caused by, or is primarily caused by, soft tissue pressure upon the inner sleeve.

In some embodiments, the robotic orienting is performed in accordance with a surgical objective.

The system or method of any previous claim wherein the robotic orienting is performed in accordance with medical imaging data.

In some embodiments, the medical imaging data comprises X-ray data and/or fluoroscopy data and/or MRI data.

In some embodiments, wherein the inner sleeve is a surgical canulla.

In some embodiments, wherein the guide sleeve and/or the surgical tool is sterilized and/or autoclavable.

In some embodiments, wherein the measurement of the lateral force is performed by a force-meter deployed in an annular region outside of the inner sleeve and within the outer sleeve.

In some embodiments, wherein the mechanical measurement of the indication of the lateral force is performed by a strain-meter configured to sense a strain upon the guide-sleeve.

In some embodiments, wherein the inner and/or outer sleeves are rigid.

A system for performing a surgical procedure at a surgical site, comprises: a. a guide-sleeve defining axial and lateral directions; b. a surgical tool movably and/or snugly disposed within the guide-sleeve so that an alignment direction of the surgical tool is determined by that of the guide-sleeve; c. a surgical robot configured to robotically orient the guide-sleeve in a target direction and/or orientation; d. a force sensor configured to measure at least one of (i) a lateral force upon the guide-sleeve or upon the surgical tool deployed therein and (ii) a mechanical indication of the lateral force (e.g. the force sensor may be configured to measure the lateral force or indication thereof in a manner that is substantially independent of a magnitude of an axial force between the surgical tool and the guide-sleeve); and e. an alert-signal-generator configured to generate an alert signal in a manner that is contingent upon a magnitude of the measured lateral force or indicator exceeding a force-threshold.

BRIEF DESCRIPTION OF THE DRAWINGS

FIGS. 1A-1B, 2-8, 9A-9D, 10A-10C, 11A-11B and 12 illustrate prior surgical tools.

FIGS. 13A-13D, and 14A-14C schematically illustrate surgical tools and systems according to some embodiments of the invention.

DETAILED DESCRIPTION OF EMBODIMENTS

Figure 1A:
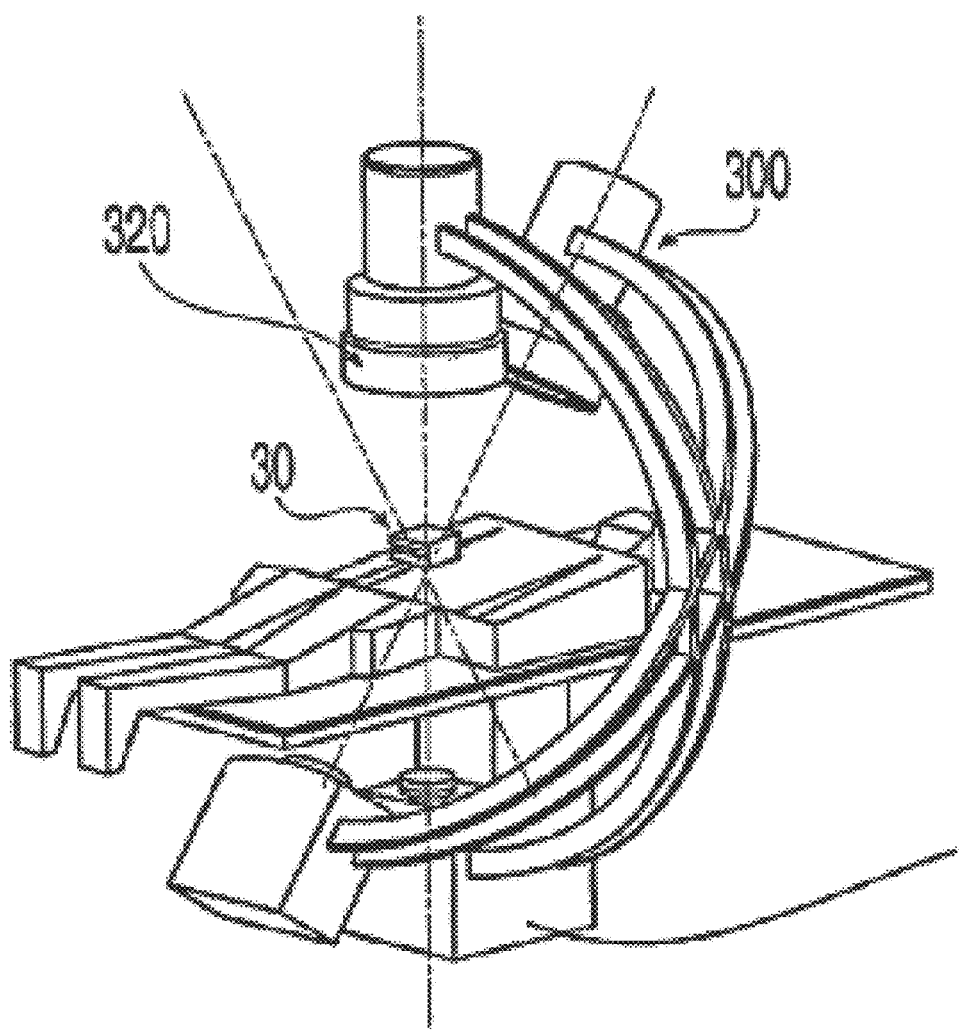
Figure 1B:
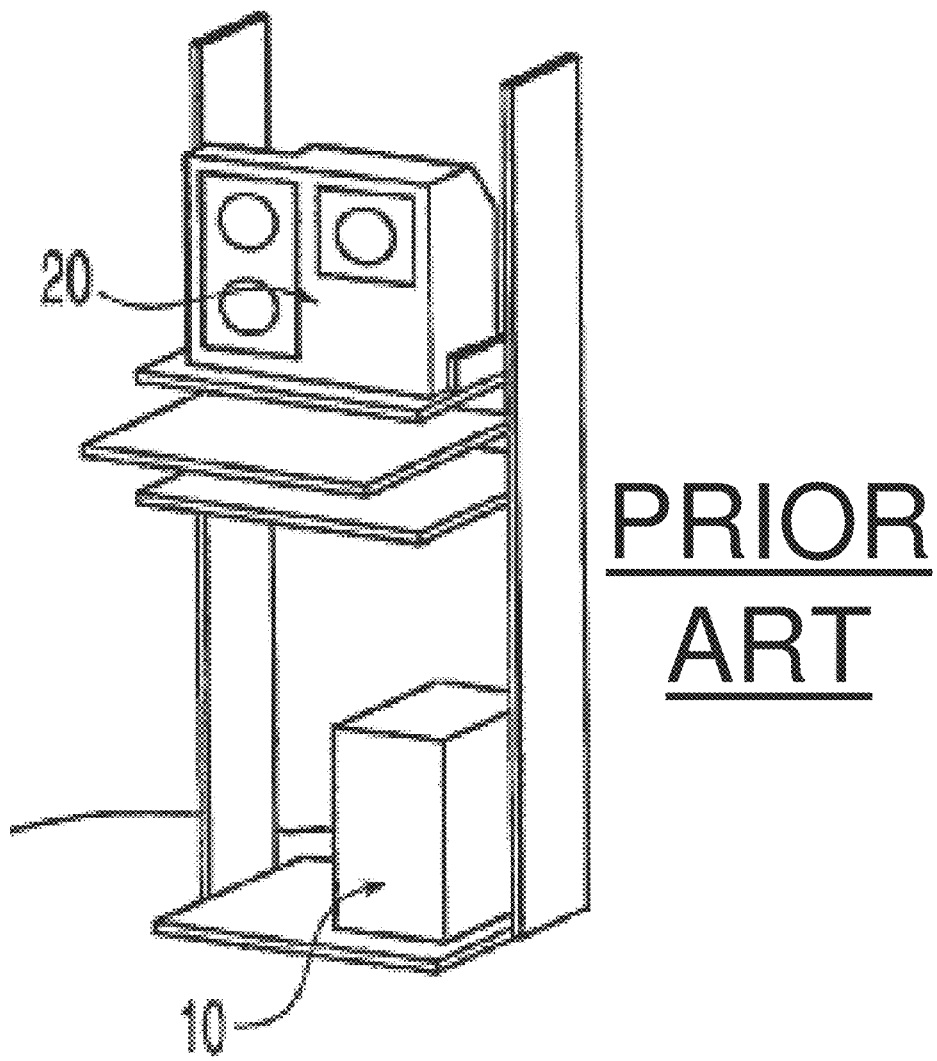
Figure 2:
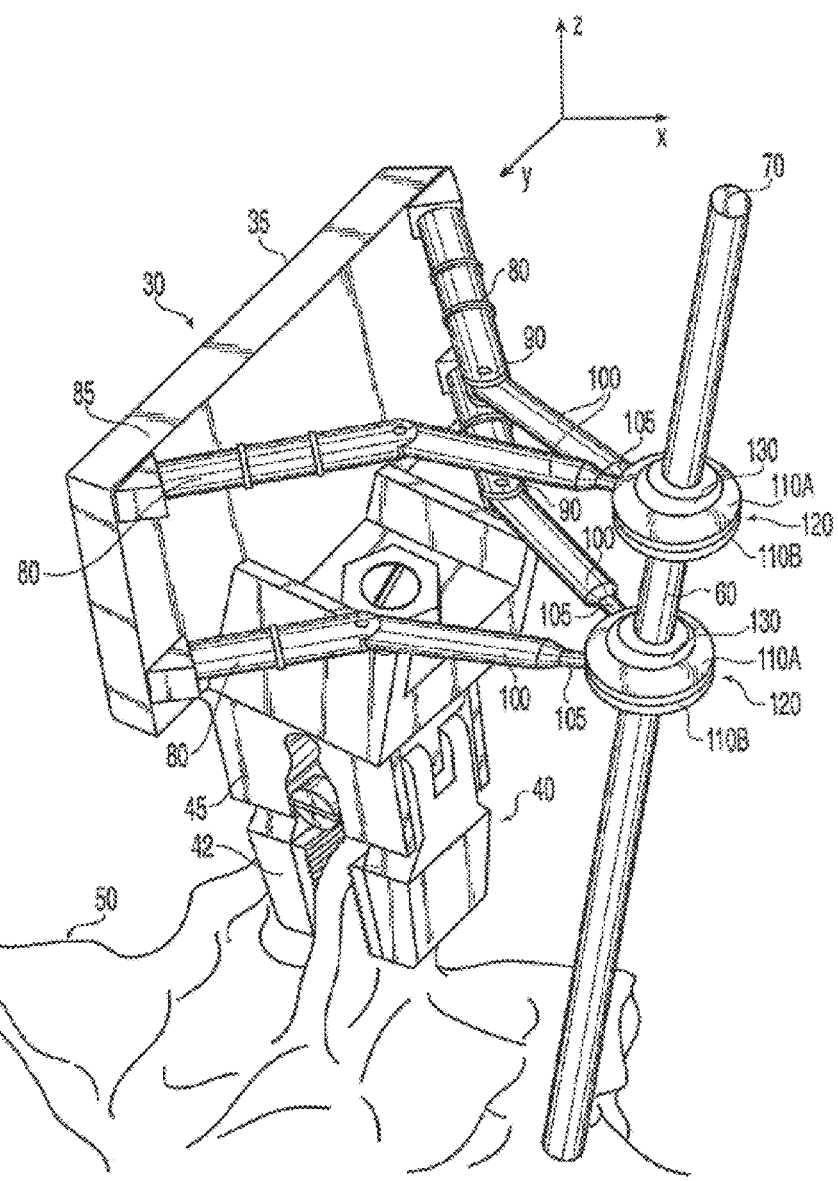
Figure 3:
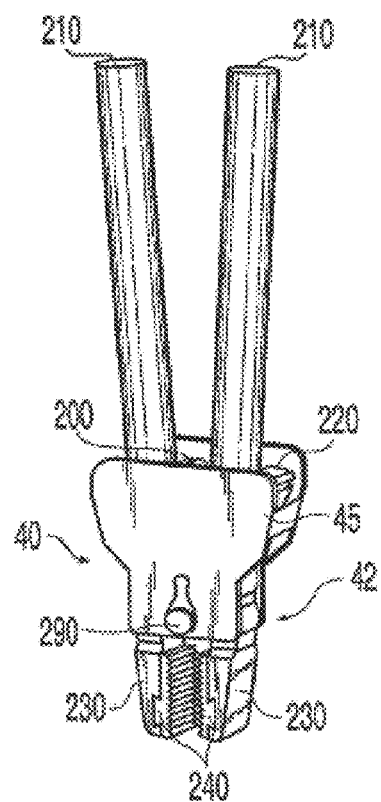
Figure 4:
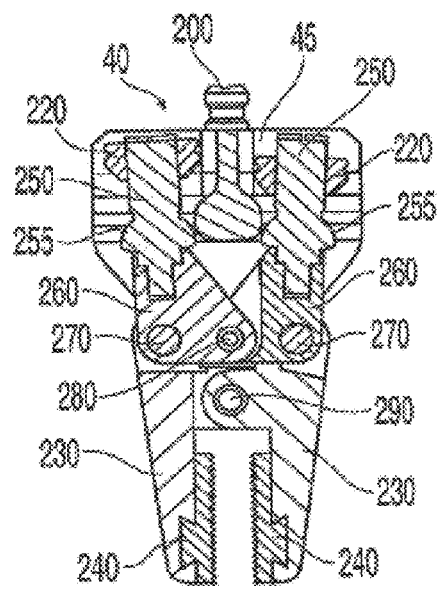
Figure 5:
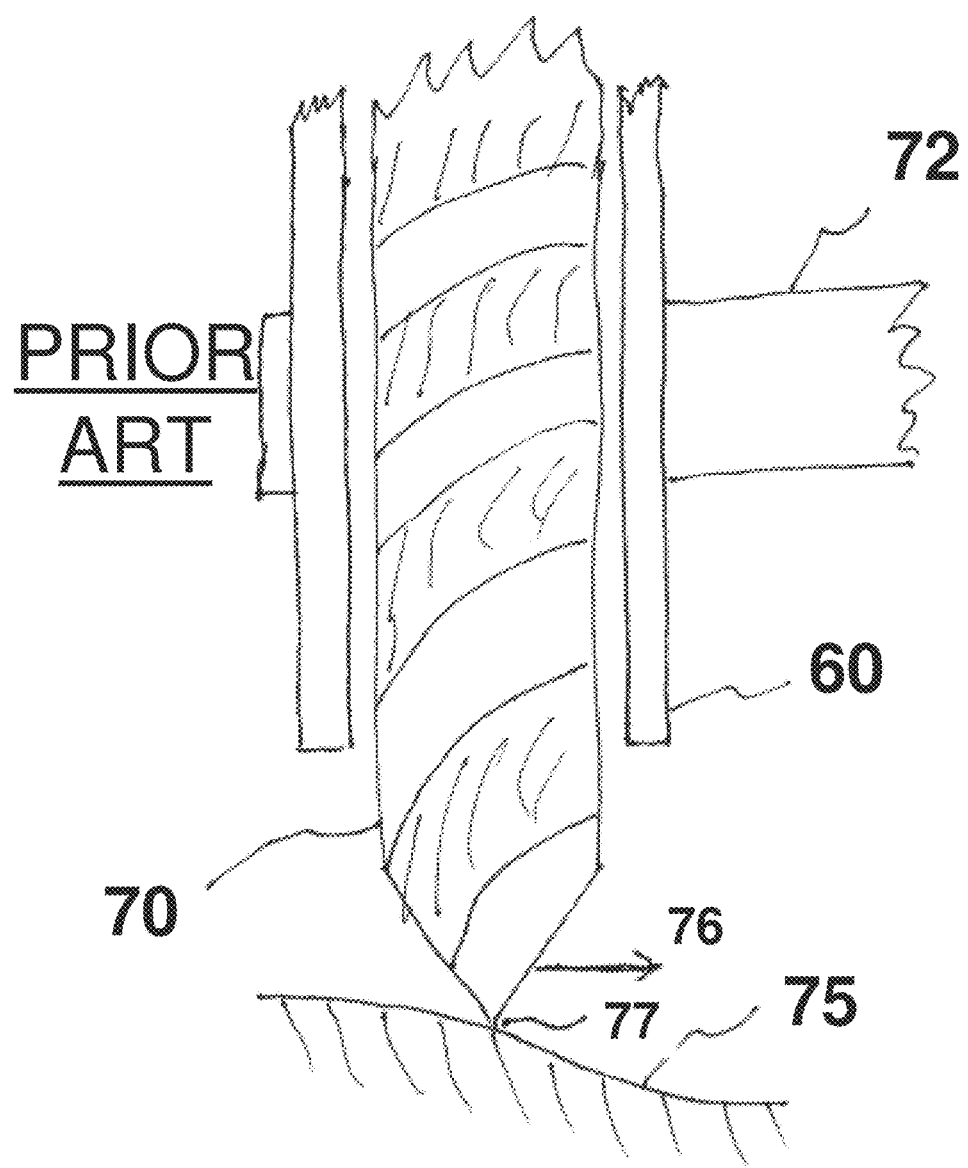
Figure 6:
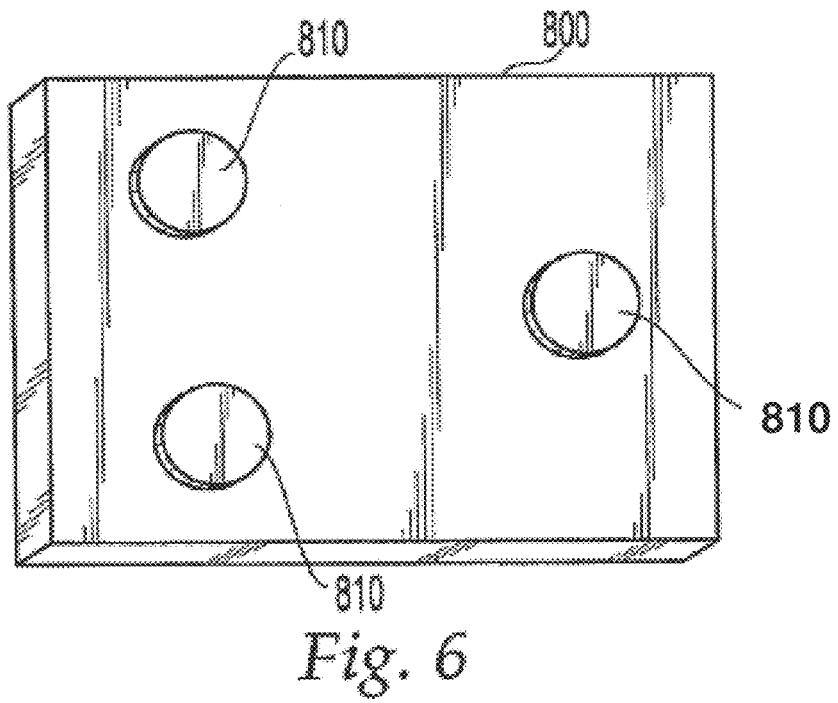
Figure 7:
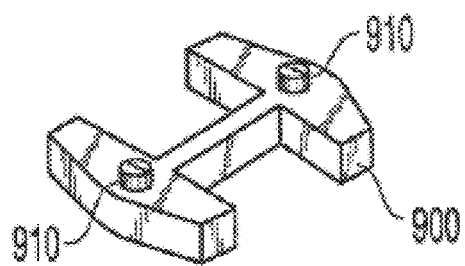
Figure 8:
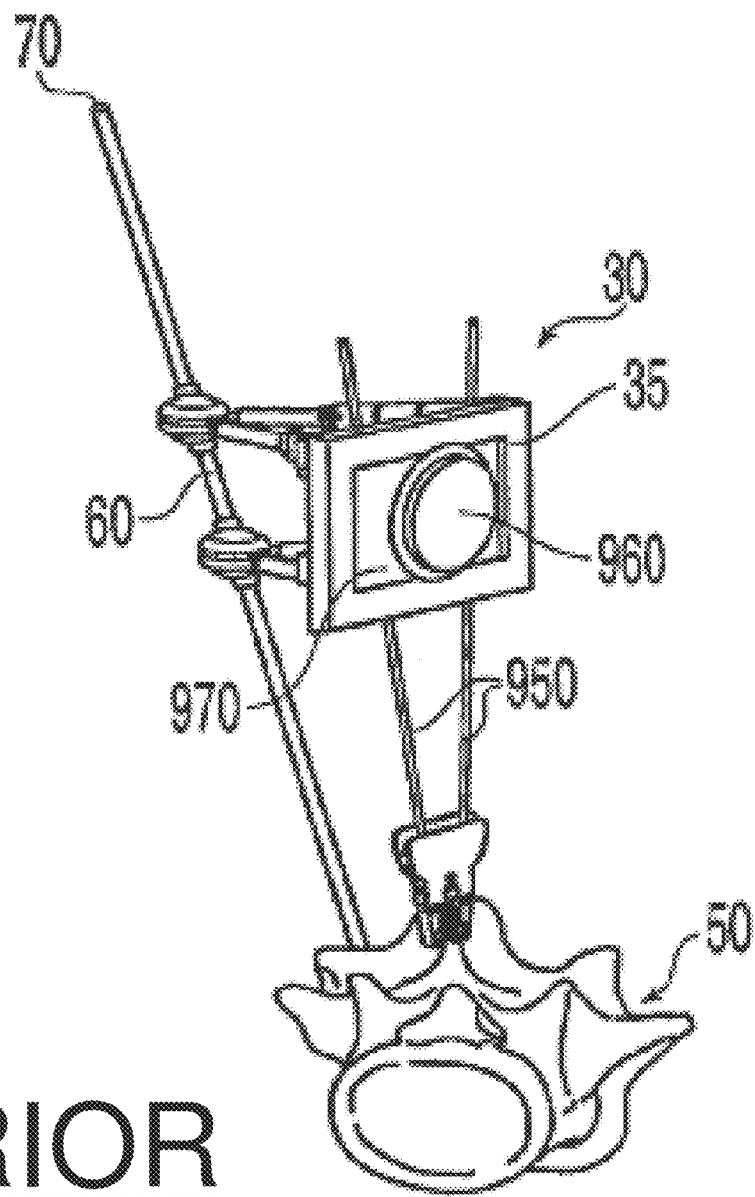
Figure 9A:
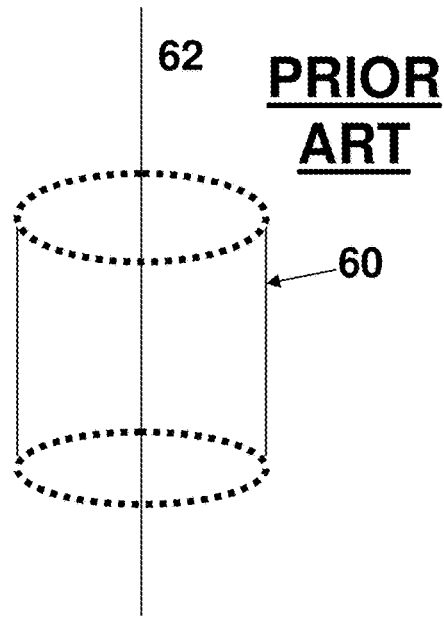
Figure 9B:
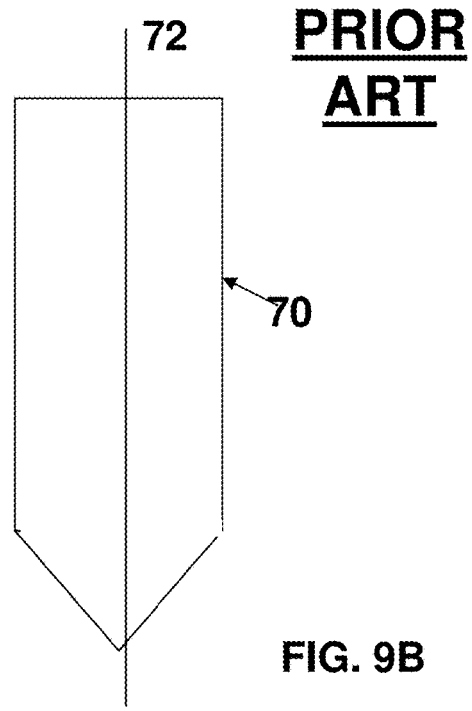
Figure 9C:
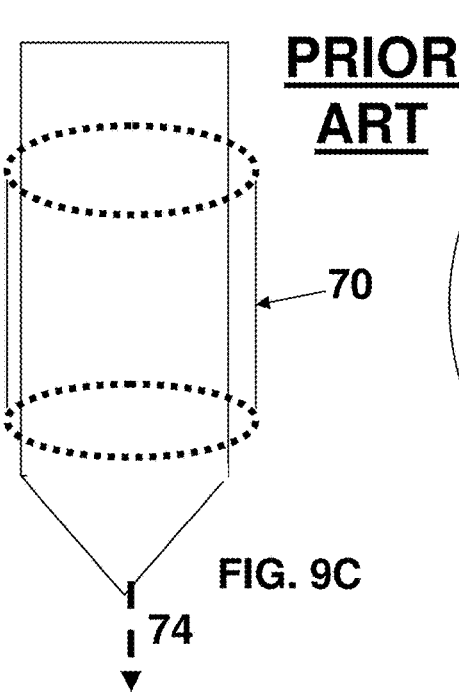
Figure 9D:
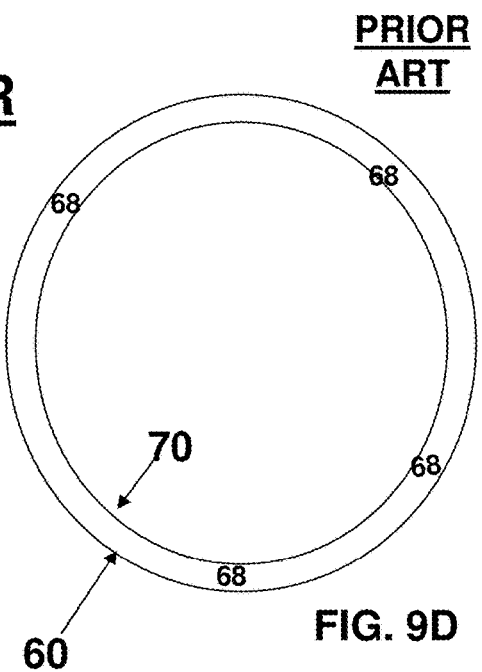

The invention is herein described, by way of example only, with reference to the accompanying drawings. With specific reference now to the drawings in detail, it is stressed that the particulars shown are by way of example and for purposes of illustrative discussion of the preferred embodiments of the exemplary system only and are presented in the cause of providing what is believed to be a useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how several forms of the invention may be embodied in practice and how to make and use the embodiments.

It should be understood that not every feature of the presently disclosed methods, apparatuses, and computer readable media having stored thereon is necessary in every implementation. It should also be understood that throughout this disclosure, where a process or method is shown or described, the steps of the method may be performed in any order or simultaneously, unless it is clear from the context that one step depends on another being performed first. As used throughout this application, the word "may" is used in a permissive sense (i.e., meaning "having the potential to"), rather than the mandatory sense (i.e. meaning "must").

Embodiments of the present invention relate to robotic surgical systems providing any feature or combination of features described above or in any of the figures.

In some embodiments, although the surgical robot computes the correct position and orientation for sleeve 60, in fact, sleeve 60 may be slightly misoriented when a lateral force is exerted upon sleeve 60. For example, the force exerted on the surgical tool 70 and/or the inner sleeve 160 may be transferred to sleeve 60. Alternatively or additionally, this force may cause (i) the support element (e.g. clamp 40 or clamping portion 42 and clamp adaptor 45) and/or (ii) the sleeve 60 and/or inner sleeve 160 or surgical instrument 70 to bend.

It is now disclosed that when sleeve 60 and/or inner sleeve 160 (e.g. canulla) and/or instrument 70 are improperly aligned, this may cause or be caused by a lateral force (i.e. in a direction perpendicular sleeve axis 62 and/or perpendicular to a direction of a planned trajectory 74 of surgical instrument). As such, a magnitude of such lateral force may be used as a marker/indicator describing a degree of misalignment between instrument 70 and sleeve 60—i.e. smaller lateral forces are indicative that sleeve 60 (or inner sleeve 160 or instrument 70) is better aligned while larger lateral forces are indicative that sleeve (or inner sleeve 160 or instrument 70) is misaligned.

When surgical tool 70 is laterally diverted from the planned trajectory by an external lateral force upon tool 70 and/or sleeve 60, this indicates that a lateral force is acting on the instrument—for example, due to skiving on the bone or by soft tissue pressure. Hence minimizing this force means that the instrument is directed along the planned trajectory.

By measuring the magnitude of the lateral force upon sleeve 60 (or an indicator thereof), it is possible to generate an alert signal if a magnitude of the lateral force exceeds a threshold value, to warn the user (e.g. a surgeon) to cease operation of instrument 70 or to refrain from operating instrument 70 due to an elevated risk that an orientation of 74 does not match the intended direction computed by the surgical robot.

It is noted that sleeve 60 and/or instrument 70 may be subject to axial forces along sleeve axis 62—e.g. a magnitude of the axial forces may significantly exceed that of the lateral forces. Thus, in some embodiments, it is desired to measure a magnitude of the lateral forces upon (or by) sleeve 60 in a manner that is substantially completely insensitive to a magnitude of a axial force along sleeve axis 62 of the guide-sleeve 60.

Many examples in the present disclosure relate to orthopedics—this is not a limitation. The presently-disclosed techniques and apparatus relate to any type of surgery including but not limited to orthopedics, neurosurgery, biopsy procedures, 'traditional' procedures, 'minimally invasive' procedures, laparoscopy or any other type of surgery.

For brevity, some explicit combinations of various features are not explicitly illustrated in the figures and/or described. It is now disclosed that any combination of the method or device features disclosed herein can be combined in any manner—including any combination of features—and any combination of features can be included in any embodiment and/or omitted from any embodiments.

Definitions

For convenience, in the context of the description herein, various terms are presented here. To the extent that definitions are provided, explicitly or implicitly, here or elsewhere in this application, such definitions are understood to be consistent with the usage of the defined terms by those of skill in the pertinent art(s). Furthermore, such definitions are to be construed in the broadest possible sense consistent with such usage.

The term 'skiving' refers to slipping by any object (e.g. a distal end of the element) in contact with a bone. The object may be a sleeve or a canulla (e.g. having teeth at a distal end thereof—e.g. as disclosed in U.S. Pat. No. 8,469,963 incorporated herein by reference) or a drill or any other object or surgical tool 70.

Some embodiments relate to 'measuring a force' or an indication thereof. Any time the term 'measuring a force' is used it may refer to 'mechanical measuring of a force'—e.g. using a force meter or a strain meter or any other instrument for measuring force. The 'mechanical' measuring of a force may optionally employ optical means (e.g. strain gauge based on photoelasticity) and electrical circuitry.

In the present disclosure 'electrical circuitry' or 'electronic circuitry' is intended broadly to describe any combination of hardware, software and/or firmware.

Electronic circuitry may include may include any executable code module (i.e. stored on a computer-readable medium) and/or firmware and/or hardware element(s) including but not limited to field programmable logic array (FPLA) element(s), hard-wired logic element(s), field programmable gate array (FPGA) element(s), and application-specific integrated circuit (ASIC) element(s). Any instruction set architecture may be used including but not limited to reduced instruction set computer (RISC) architecture and/or complex instruction set computer (CISC) architecture. Electronic circuitry may be located in a single location or distributed among a plurality of locations where various circuitry elements may be in wired or wireless electronic communication with each other.

A 'position/orientation' controller is a device configured to determine or regulate changes in at least one of (i) a position of guide-sleeve 60 and/or (ii) an orientation of guide-sleeve 60—for example, to a target portion and/or orientation. The position/orientation controller may by automated (e.g. a surgical robot—for example, including one or more motors) or may be a manual or passive guidance system where the mechanical force for moving and/or orienting the guide-sleeve is supplied manually. One example of a 'manual' or 'passive' guidance system is a frame-based or track-based system such as a stereotactic-based system comprising a stereotactic frame where the guide-sleeve moves along a frame or track.

A 'robot' may include a robot controller and/or 'electronic circuitry'—for example, to compute any quantity—e.g. a position and/or orientation of sleeve 60 or any other quantity. A robot is an example of a position/orientation controller.

A 'guide-sleeve' is any sleeve where it is intended to deploy an inner sleeve or a surgical instrument therein. The guide sleeve may define axial and lateral directions according to sleeve axis 62.

A force 'between' objects A and B (e.g. a lateral force) is any one of (i) a force applied by A upon object B; and (ii) a force applied by object B upon object A. A force 'between' objects A and B may be applied directly or indirectly via one or more additional object(s).

In some embodiments, ' substantially completely insensitive to a magnitude of a axial force' means that the measured value of the lateral force (or indication thereof) increases by at most 10% (or at most 5% or at most 1%) in response to a 100% increase in a magnitude of axial forces upon sleeve 60 or sleeve 160 or instrument 70.

One example of a device that may be used to measure a magnitude of lateral force applied upon sleeve 60 by instrument 70 (or by sleeve 60 upon instrument 70) is a force meter 155 deployed in annular region 68—see FIGS. 13A-13B. In another example, it is possible to utilize the fact that the lateral force exerted by the inner sleeve upon the outer sleeve deforms the outer sleeve. Thus, in a second example and referring to FIGS. 13C-13D, it is possible utilize strain-meter 165 to measure the strain upon the outer sleeve 60 as an indicator of a magnitude of the lateral force by or upon sleeve 60. In this case the sensor can be located either on the inner surface or outer surface of the sleeve.

The skilled artisan will appreciate that although the sleeve 60 and tool 70 are illustrated as being cylindrical in shape, this is not a requirement, and other shapes may be used.

A 'skiving detector' comprises any combination of mechanical or electrical or optical or other components configured to detect at least one of a presence or absence or skiving between an (i) object (e.g. guide-sleeve 60 or instrument 70 such as an inner sleeve) and (ii) a bone of the patient.

An 'alert-signal-generator' comprises any of mechanical or electrical or optical or other components for generating a contingent alert signal—e.g. a visual alert signal or an audio alert signal or any other alert signal.

Figure 14A:
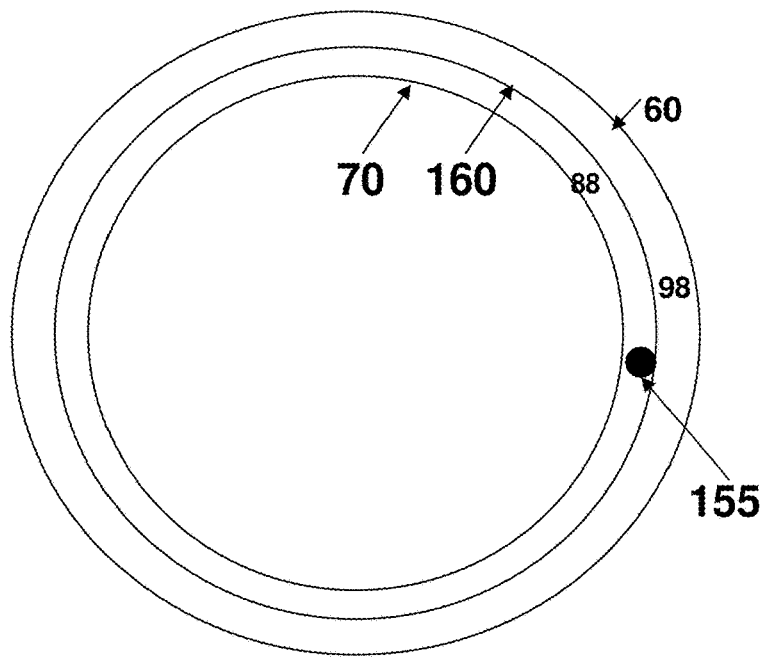
Figure 14B:
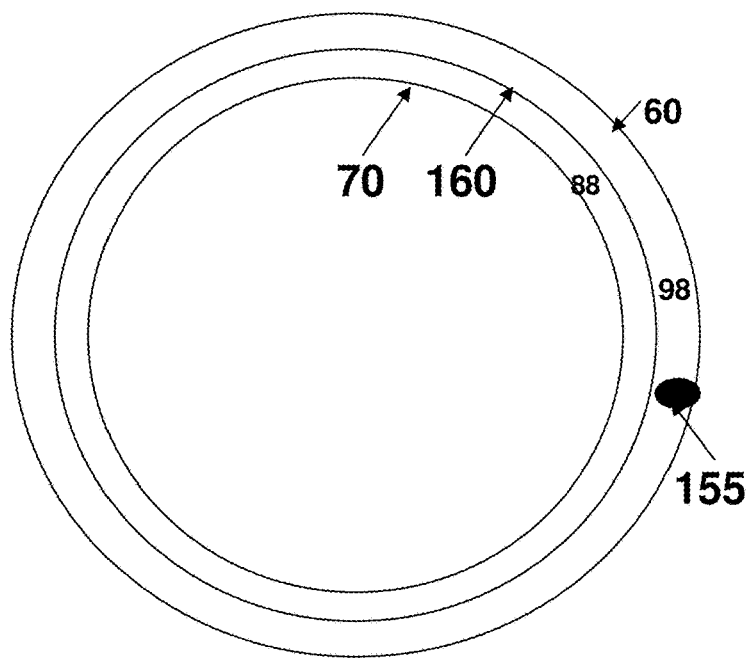
Figure 14C:
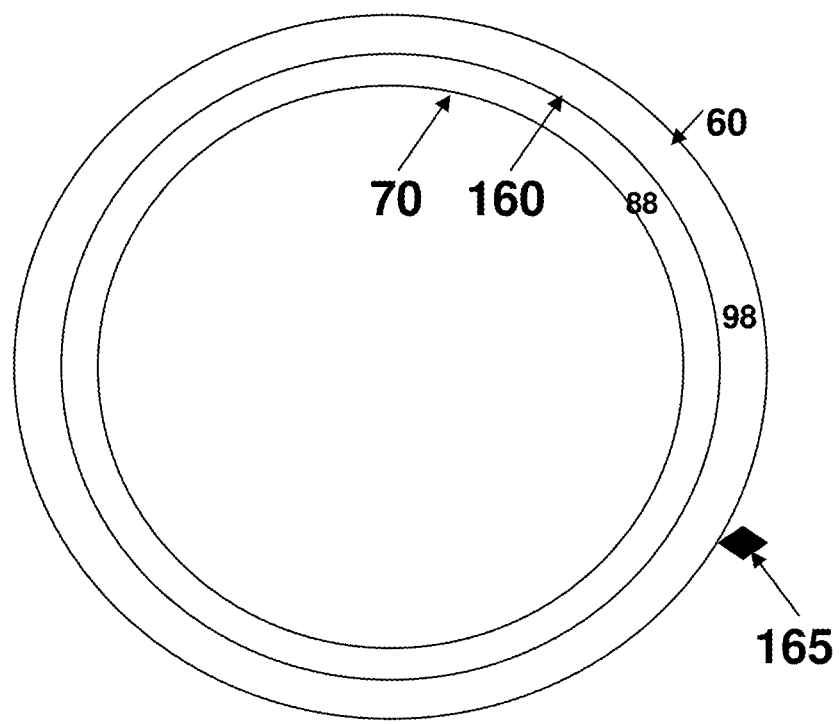

The skilled artisan will appreciate that various elements in FIGS. 13A-13D and in FIGS. 14A-14C are illustrated schematically—for example, there is no requirement for a force meter 155 or strain mater 165 to have oval or diamond shapes. These are merely schematic symbols.

Figure 10A:
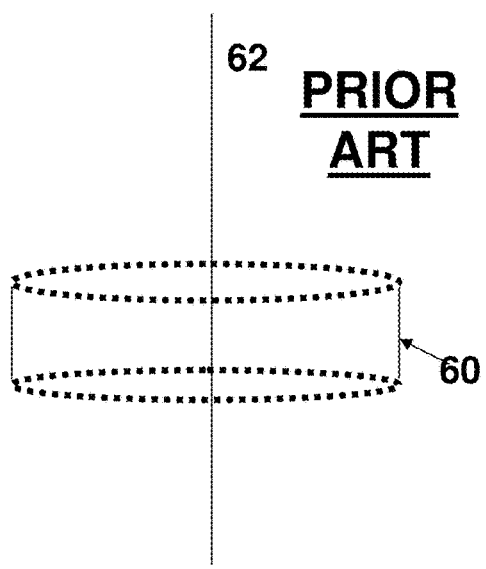
Figure 10B:
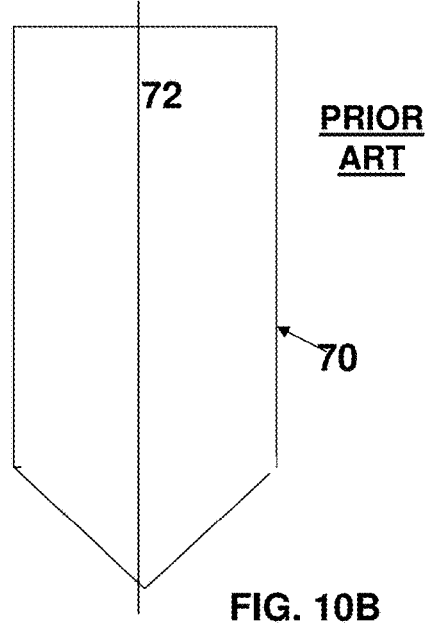
Figure 10C:
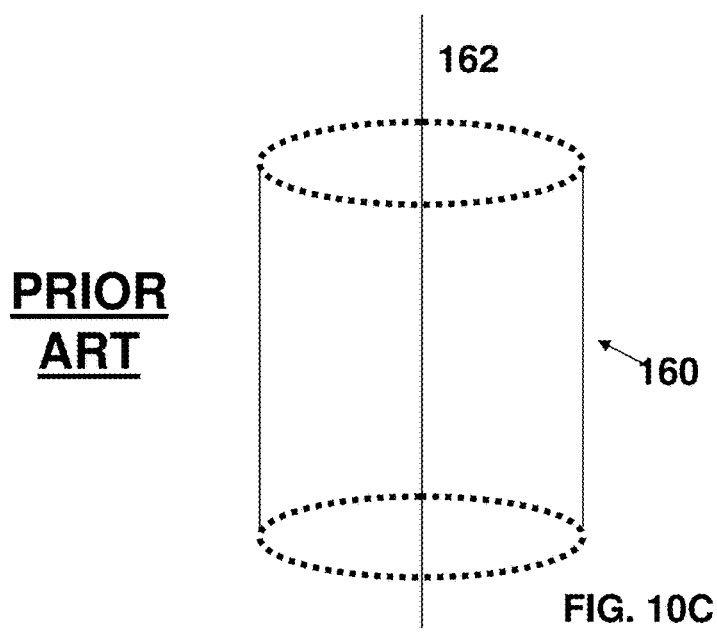
Figure 12:
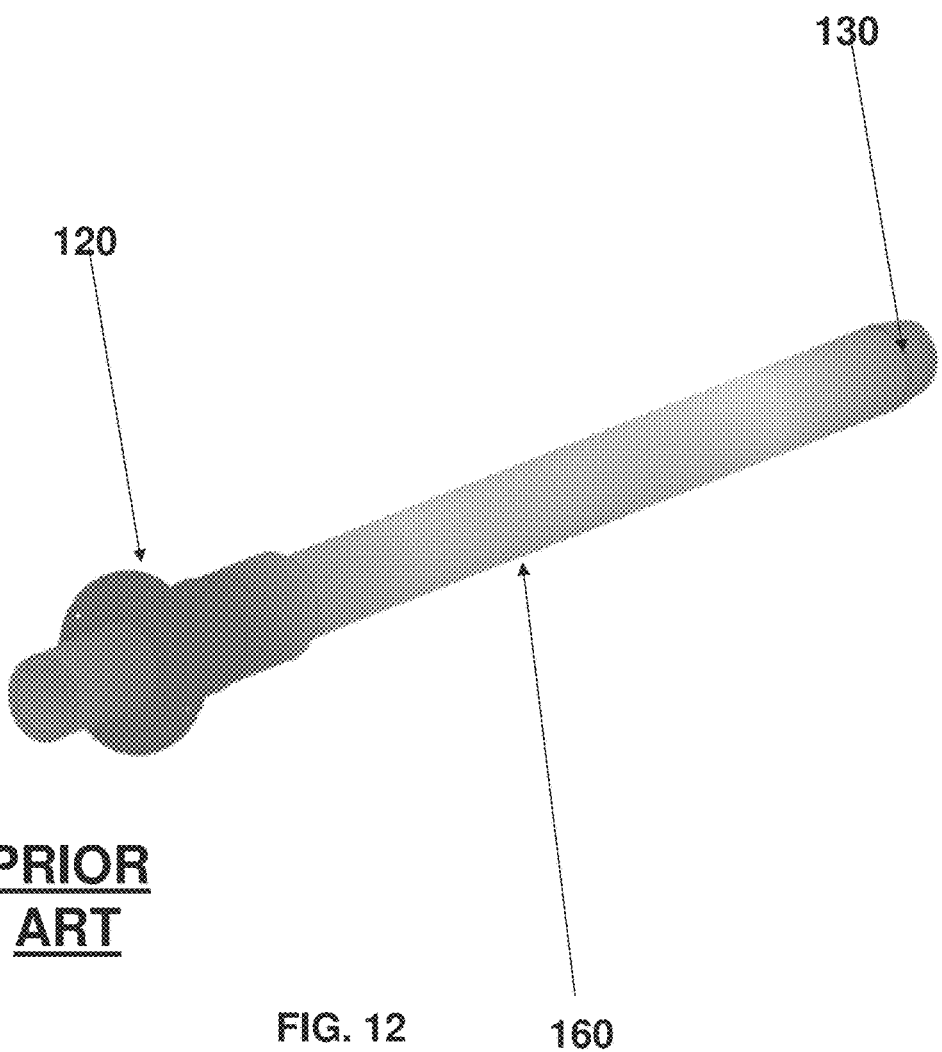

FIGS. 14A-14C refer to the devices for directly or indirectly sensing lateral force by or upon sleeve 60 in the system described above with reference to FIGS. 10-11. For brevity, only top views are shown.

In FIG. 14A a force sensor 155 is deployed in annular region 88—for example, to sense a force applied by instrument 70 upon sleeve 60 via inner sleeve (e.g. canulla) 160.

In FIG. 14B a force sensor 155 is deployed in annular region 88—for example, to sense a force applied by sleeve 160 upon sleeve 60 and/or applied by instrument 70 upon sleeve 60 via inner sleeve (e.g. canulla) 160. For example, a distal end of sleeve 160 (e.g. canulla) may be in contact with the bone and may be skiving.

FIG. 14C includes strain sensor 165 and is analogous to FIG. 13D.

Figure 15:
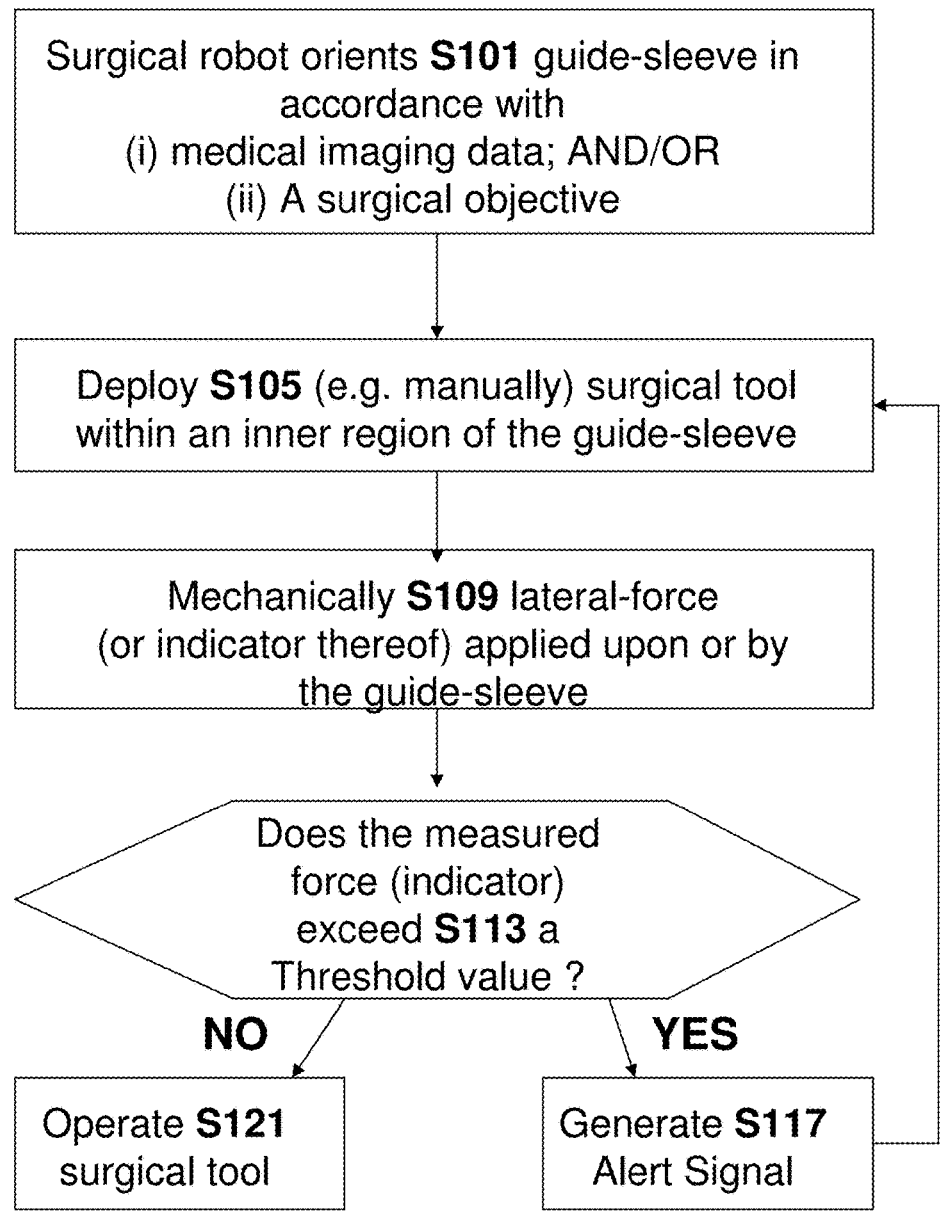
FIGS. 15-16 are flow charts of methods according to some embodiments of the invention.
Figure 16:
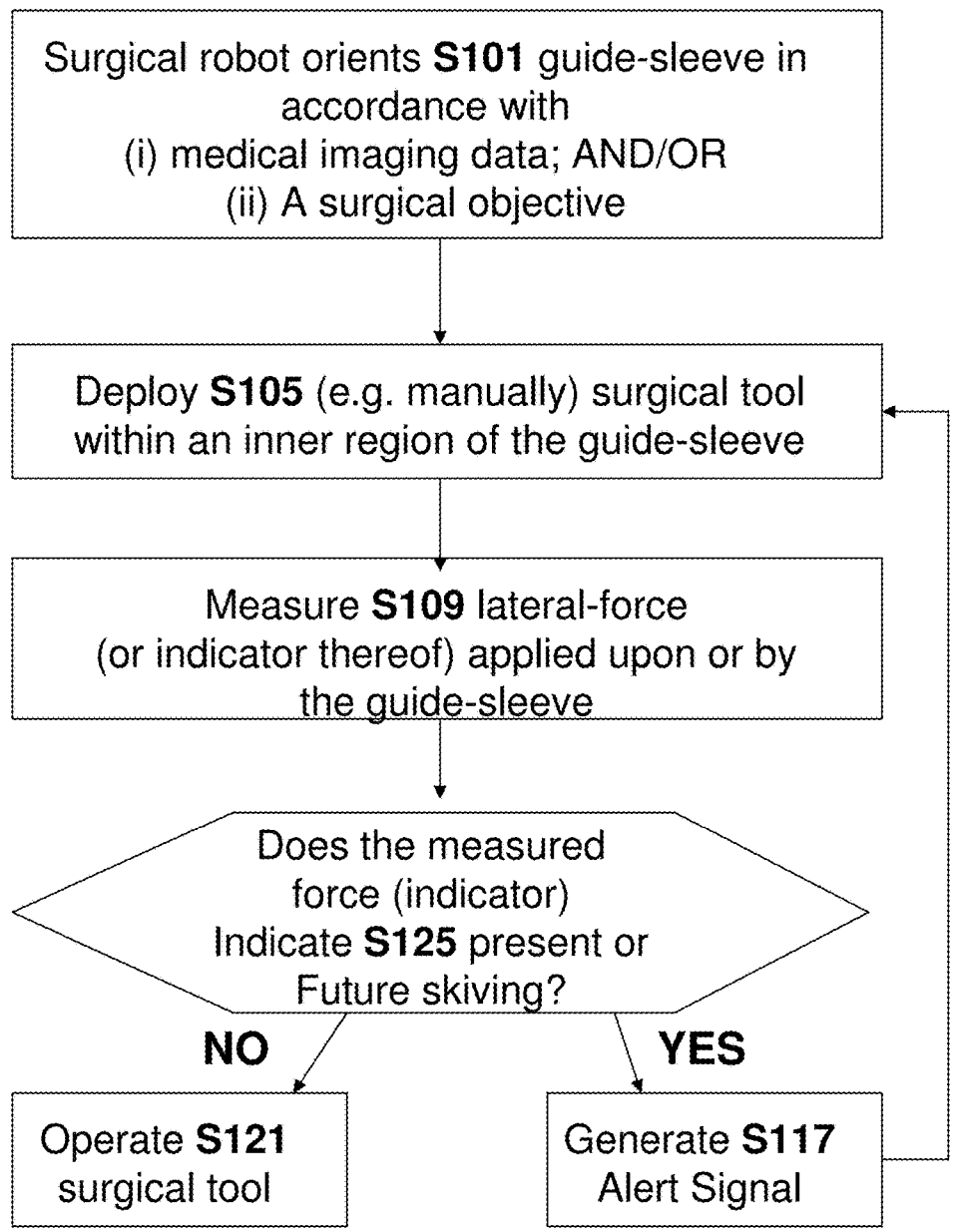

FIGS. 15-16 are flow charts of methods according to some embodiments of the invention.

FIG. 15 is a flow-chart of a method for responding to lateral forces applied by or upon sleeve 60. FIG. 16 relates to responding to detected or predicted skiving.

For both figures, in step S101, a surgical robot orients sleeve 60 in accordance with (i) medical imaging data (e.g. CT data) and/or (ii) a surgical objective—e.g. to drill into a target bone. In step S105, the user deploys (e.g. by manual insertion or automatically) a surgical tool 70 (or an inner sleeve 160) into guide-sleeve 60—e.g. so that the tool 70 is deployed snugly and/or movably within guide-sleeve 60.

In step S109, lateral-force by or upon guide-sleeve 60 is measured. In the event that a magnitude of the lateral force exceeds some sort of threshold value S113 (e.g. indicative of present or future skiving by canulla 160 or surgical instrument 70—see step S125 of FIG. 16), then an alert signal is generated S117—e.g. an audio or a visual alert signal or any other kind of alert signal. In this case, the user may elect remove and re-deploy surgical tool 70 within guide sleeve 60.

In the absence of any alert signal, this may indicate that an orientation of axes 62, 72 and 'operation direction' 74 is according to the planned direction assuming that relevant elements (robot, registration algorithm etc.) established when orienting sleeve 60 by the surgical robot. In this case, the user may elect, in the absence of the alert signal, to operate tool 70 in step S121.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

All references cited herein are incorporated by reference in their entirety. Citation of a reference does not constitute an admission that the reference is prior art.

The articles "a" and "an" are used herein to refer to one or to more than one. (i.e., to at least one) of the grammatical object of the article. By way of example, "an element" means one element or more than one element.

The term "including" is used herein to mean, and is used interchangeably with, the phrase "including but not limited" to.

The term "or" is used herein to mean, and is used interchangeably with, the term "and/or," unless context clearly indicates otherwise.

The term "such as" is used herein to mean, and is used interchangeably, with the phrase "such as but not limited to".

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons skilled in the art.

What is claimed is:

1. A system for performing a surgical procedure at a surgical site, the system comprising:
    a. a guide-sleeve defining axial and lateral directions;
    b. a surgical tool movably and/or snugly disposed within the guide-sleeve so that an alignment direction of the surgical tool is determined by that of the guide-sleeve;
    c. a skiving-detector configured to detect current and potential tool-bone skiving by the surgical tool, according to a magnitude of a lateral force between the surgical tool and the guide-sleeve or according to an indication of the lateral force magnitude;
    d. a position/orientation controller configured to use a comparison of any said detection to a threshold to predict skiving, wherein said threshold is selected to indicate an elevated risk of skiving; and e. an alerter configured to generate an alert signal upon a positive current detecting of skiving, or a positive predicting of skiving.

2. A method of preventing misalignment of a surgical instrument during its operation, said surgical instrument used to perform a surgical procedure at a surgical site, the method comprising:

a. orienting and/or positioning a guide sleeve in a target orientation, said surgical instrument movably and/or snugly disposed within said guide-sleeve so that an alignment direction of said surgical tool is determined by that of said guide-sleeve;

b. at a time when the surgical instrument is disposed within the guide sleeve, measuring, using a skiving-detector configured to detect current and potential tool-bone skiving by said surgical instrument, a magnitude of a lateral force between said surgical instrument and said guide sleeve or an indication of the lateral force magnitude;

c. contingent upon the results of the measuring indicating that the lateral force magnitude or said indication thereof exceeds a threshold selected to indicate an elevated risk of skiving, generating an alert signal to indicate a positive current detecting of skiving, or a positive predicting of skiving; and d. if said alert signal is generated, refraining from operation of said surgical instrument.

3. The method of claim 2 wherein the orienting and/or positioning of the guide sleeve is performed robotically.

4. The method of claim 2 wherein the magnitude of the lateral force is indicative of at least one of a (i) a degree of bone flexibility; and (ii) a degree of flexibility by of the mounted object upon which the surgical robot is mounted on the bone.

5. The method of claim 2 wherein the surgical instrument is a surgical cannula.

6. The method of claim 2 wherein the surgical instrument comprises at least one of: (i) a plurality of teeth at a distal end thereof and (ii) a knurled knob at a proximal end thereof.

7. The method of claim 2 wherein the surgical tool instrument is selected from the group consisting of a drill, a reamer, a biopsy needle, forceps and an endoscope.

8. The method of claim 2 wherein the lateral force is at least partially caused by, or is primarily caused by, soft tissue pressure upon an inner sleeve within the guide sleeve.

9. The method of claim 8 wherein the inner sleeve is a surgical cannula.

10. The method of claim 2 wherein the measurement of the lateral force is performed by a force-meter deployed in an annular region outside of the inner sleeve and within the outer sleeve.

11. The method of claim 2 wherein the measurement of the indication of the lateral force is performed by a strain-meter configured to sense a strain upon the guide-sleeve.

12. The system of claim 1 wherein the skiving-detector comprises a strain-meter configured to sense a strain upon the guide-sleeve.

13. The system of claim 12, wherein said strain-meter is disposed on the outer surface of said guide-sleeve, and wherein said indication of said lateral force is a measurement of strain upon said outer surface of said guide-sleeve.

14. The method of claim 11, wherein said strain-meter is disposed on the outer surface of said guide-sleeve and wherein said indication of said lateral force is a measurement of strain upon said outer surface of said guide-sleeve.

15. The method of claim 2, wherein said elevated risk of skiving is an elevated risk that the orientation of said surgical instrument does not match said target orientation.

* * * * *